United States Patent
McGrath et al.

(10) Patent No.: US 6,567,495 B2
(45) Date of Patent: May 20, 2003

(54) DETECTOR HAVING PROGRAMMABLE SLICE THICKNESS AND OPERATIONAL MODES AND METHOD

(75) Inventors: Donald Thomas McGrath, Clifton Park, NY (US); David Michael Hoffman, New Berlin, WI (US)

(73) Assignee: General Electric Company, Niskayuna, NY (US)

( * ) Notice: Subject to any disclaimer, the term of this patent is extended or adjusted under 35 U.S.C. 154(b) by 114 days.

(21) Appl. No.: 09/799,173

(22) Filed: Mar. 6, 2001

(65) Prior Publication Data

US 2002/0126795 A1 Sep. 12, 2002

(51) Int. Cl.[7] .............................................. G01N 23/00
(52) U.S. Cl. .......................................... 378/19; 348/308
(58) Field of Search ................................ 378/19, 12, 4, 378/901, 98.8; 250/584, 332, 553; 348/302, 308, 294

(56) References Cited

U.S. PATENT DOCUMENTS 6,198,791 B1 * 3/2001 He et al. ....................... 378/19

* cited by examiner

Primary Examiner—Drew A. Dunn
Assistant Examiner—Irakli Kiknadze
(74) Attorney, Agent, or Firm—John F. Thompson; Patrick K. Patnode

(57) ABSTRACT

A detector device used in an imaging system includes a photodiode array that is positioned to detect radiation transmitted by the imaging system. A switch array is connected to the photodiode array. The switch array has an output and comprises switch banks having switches. A control logic circuit is connected to the switch array and controls the state of the switches in the switch banks based on a predefined switching configuration. The control logic circuit also includes a memory device programmed to store the predefined switching configurations. The predefined switching configurations represent respective operational modes of the imaging system wherein each respective operational mode has a respective predetermined detector slice thickness.

39 Claims, 5 Drawing Sheets

DETECTOR HAVING PROGRAMMABLE SLICE THICKNESS AND OPERATIONAL MODES AND METHOD

BACKGROUND OF THE INVENTION

The present invention relates to detectors used in medical imaging systems, and more particularly, to detectors having programmable slice thickness and/or operational modes implemented via switching configurations stored in a memory device.

Typically in medical imaging systems, such as, for example, computed tomography (CT) systems, the system includes a detector comprising an array of photodiodes that detect radiation, such as, for example, x-rays, that are emitted from a radiation source. During detection of the radiation, it is desired that the radiation be collimated. When the radiation is collimated, the slice thickness of the radiation detected by the array of photodiodes of the detector can be controlled more easily. The collimated radiation is desired during various imaging techniques, during service of the detector and/or medical imaging system and during the performance of various experimental techniques.

In some medical imaging systems, the radiation is collimated using structural collimators that are placed on or near the detector. The structural collimators ensure that any radiation that is directed toward the array of photodiodes of the detector is parallel. These structural collimators are used not only to ensure that the radiation is parallel, but the structural collimators also control the slice thickness of the radiation detected by the array of photodiodes. However, structural collimators have some limitations. For example, a different structural collimator has to be fabricated for each slice thickness that is desired. In addition, to change the slice thickness, the structural collimator having the desired slice thickness must be installed in the medical imaging system. Installation of different structural collimators involves discontinuing operation of the medical imaging system for a prolonged period of time while a different structural collimator is installed.

In other medical imaging systems, the photodiode array of the detector is connected to a plurality of switches, such as, for example, transistors. The state of each of the plurality of switches is controlled such that specified photodiodes in the array of photodiodes are used to detect the radiation. The selection of the specified photodiodes also controls, among other things, the slice thickness of the radiation detected by the array of photodiodes of the detector. In the medical imaging systems that use switches connected to the photodiode array, a predetermined number of switching configurations is hardwired via a multiplexer to the switches, the switching configurations control the plurality of switches. Each of these switching configurations represents a different operational mode of the medical imaging system. However, these hardwire multiplexed-type medical imaging systems have some limitations. For example, the number of operational modes of these medical imaging systems is limited to the predetermined number of switching configurations that are hardwired to the multiplexer. For new operational modes or new switching configurations to be added to these medical imaging systems, the multiplexer must be re-wired to add the switching configuration and/or the operational mode to the medical imaging system. In addition, the re-wiring of the multiplexer to add switching configurations requires the medical imaging systems to be shut down for a prolonged period of time until the switching configurations are reconfigured.

Therefore, it is desired that a medical imaging system be produced having a programmable slice thickness that does not require fabrication or installation of structural elements and/or rewiring of the control electronics. Further, it is also desired that a medical imaging system be produced that can be re-programmed with new operational modes and/or new switching configurations without discontinuing operation of the medical imaging system for a prolonged period of time.

BRIEF SUMMARY OF THE INVENTION

In one exemplary embodiment, a detector device for use in an imaging system is provided. The detector device comprises a photodiode array positioned to detect radiation transmitted by the imaging system. A plurality of switch arrays is connected to the photodiode array. Each of the plurality of switch arrays has at least one output. In addition, each of the plurality of switch arrays comprises a plurality of switch banks wherein each of the plurality of switch banks includes a plurality of switches. A control logic circuit is connected to the plurality of switch arrays and controls the state of each of the plurality of switches in each of the plurality of switch banks based on a predefined switching configuration. The control logic circuit comprises a memory device that is programmed to store a plurality of predefined switching configurations. Each of the plurality of predefined switching configurations represents a respective operational mode of the imaging system. Additionally, each respective operational mode has a respective predetermined detector slice thickness.

In another exemplary embodiment, a method for selecting a slice thickness of a photodiode array of a detector in an imaging system is provided. The method comprises providing a plurality of switches connected to a detector. A plurality of switching configurations are defined wherein each of the plurality of switching configuration represents an operational mode of the imaging system. A memory device stores a plurality of switching configurations. Each of the plurality of switching configurations represents a respective operational mode of the imaging system. In addition, each respective operational mode has a respective predetermined detector slice thickness. One of the plurality of operational modes of the imaging system is selected. A corresponding switching configuration is retrieved, and the corresponding switching configuration relates to the selected one of the plurality of operational modes. The state of each of the plurality of switches is configured according to the corresponding switching configuration. The desired operational mode of the imaging system is performed with the switches configured in the retrieved switching configuration.

DETAILED DESCRIPTION OF THE INVENTION

Figure 1:
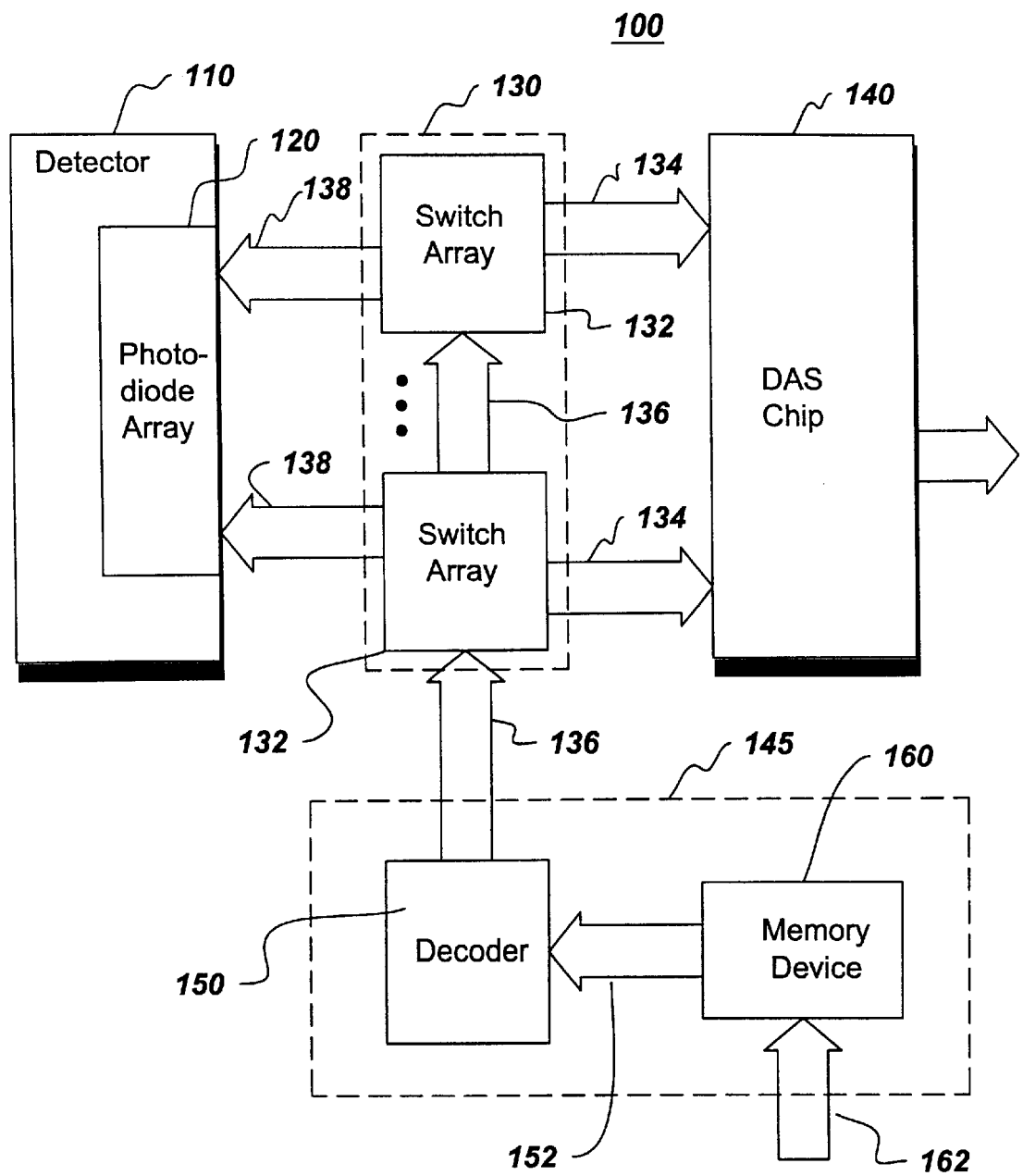
FIG. 1 is a schematic box diagram view of one representative embodiment of a programmable slice thickness detector.

In FIG. 1, a highly simplified view of an imaging system 100 includes a detector 110 having a photodiode array 120.

In one embodiment, the imaging system 100 comprises a medical imaging system. In another embodiment, the imaging system 100 comprises a computed tomography (CT) imaging system. The imaging system 100 includes a radiation source (not shown) that emits radiation. The emitted radiation is transmitted through various body parts of a patient. The transmitted radiation is collected by the photodiode array 120 of the detector. The photodiode array 120 is connected to a plurality 130 of switch arrays 132 via photodiode connection 138. In one embodiment, the plurality 130 of switch arrays 132 are controlled by a control logic circuit 145 that includes a memory device 160. In one embodiment, the memory device 160 stores a plurality of switching configurations wherein each of the plurality of switching configurations relates to an operational mode of the imaging system 100. In one embodiment, the operational mode of the imaging system 100 relates to various uses of the imaging system, such as, for example, experimental use, service use and imaging use.

In addition, the control of the plurality 130 of switch arrays 132 also controls which photodiodes of the photodiode array 120 that are used to collect the radiation. The radiation is collimated on the detector 110 via collimator (not shown). It should also be appreciated that the switching configurations control the slice thickness of the detector 110 by controlling which of the photodiodes of the photodiode array 120 are actively being used to collect radiation during operation of the desired operational mode. As such, by controlling the on/off state of the switches 332 (FIG. 3) in the switching arrays 132 the slice thickness of the detector 110 can be controlled. Also, the switching configurations control the information that is provided to data acquisition system (DAS) chip 140 in response to the transmitted radiation received by the detector 110. In one embodiment, the DAS chip 140 receives the signals, such as, for example, current or voltage signals, that are generated by the photodiodes of the photodiode array 120. The DAS chip 140, further, can convert the signals into digital data that is further processed and/or evaluated to produce a medical image. More specifically, the switching configurations control which photodiodes of the photodiode array 120 provide information to the DAS chip 140 by selectively turning on/off the switches 332 (FIG. 3) in the switching arrays 132 connected to the photodiode array 120 via the photodiode connection 138. In this manner, a user of the imaging system 100 can select from various operational modes of the imaging system 100 while the operational modes can easily be upgraded or changed by reprogramming the memory device 160 with new and/or different switching configurations. As such, the switching configurations and the operational modes of the imaging system 100 can be made programmable via hardware or software connected to the imaging system 100.

As further shown in FIG. 1, the control logic circuit 145 includes memory device 160 that receives mode select input 162. It should be appreciated that, in one embodiment, the memory device 160 comprises a random access memory (RAM). It should also be appreciated that, in other embodiment, the memory device 160 can comprise various storage device, such as, for example, a magnetic media, read-only memory (ROM), programmable read-only memory (PROM), erasable programmable read-only memory (EPROM), electrically erasable programmable read-only memory (EEPROM). In one embodiment, the mode select input 162 can be provided from an external computing device (not shown), or in another embodiment, the mode select input 162 can be provided from a computing device (not shown) integral with the imaging system 100. The memory device 160 provides a control signal output 152 to decoder 150. In one embodiment, where memory device 160 is directly mapped to each of the switches 332, the decoder 150 comprises connected (not shown) that connect the memory device 160 to each of the switches 332. In another embodiment, the decoder 150 includes combinatorial logic that receives data from the memory device 160 and converts that data into a switching configuration that controls the state of each of the switches 332 or each switching array 132. In one aspect of this embodiment, the memory device 160 stores six (6) bits of information that represent $2^6$ or 64 possible states while the switching array 132 comprises 42 independent switches and each of the plurality 130 of switching arrays 132 has eight (8) switching banks 330 per each switching array 132. As stated hereinabove in one embodiment, the memory device 160 stores a plurality switching configurations. In another embodiment, the memory device 160 stores at least one switching configuration. In any case, the switching configuration stored in the memory device 160 is provided to the decoder 150 that decodes the switching configuration information. In one embodiment, decoding the switching configuration information converts a first number of control signal outputs 152 to a second number of control output 136, wherein the first number is less than the second number, such that the switches 332 (FIG. 3) of the switching arrays 132 are controlled. In another embodiment, the memory device 160 can be directly connected each switch 332 (FIG. 3) in the switch arrays 132. In this embodiment, control signal output 152 of the memory device 160 is directly connected to the switching arrays 132 with or without the use of a decoder 150. In addition, in this embodiment, the individually connected switches 332 (FIG. 3) in each switch array 132 are directly mapped to the memory device 160, and each has a unique memory address. Further, in this embodiment, the memory device 160 has a number of connects to the switch arrays 132 that is equal to the number of switches 332 (FIG. 3) in the plurality 130 of switch arrays 132.

As shown in FIG. 1, the control output 136 is connected to each switch array 132. It should be appreciated that, in one embodiment, the plurality 130 of switch arrays 132 comprises sixteen (16) switch arrays 132 that are each connected via the control output 136 to decoder. As stated hereinabove, each of the switch arrays 132 is connected to the photodiode array 120. In addition, each switch array 132 is connected to the DAS chip 140 via switch array output 134. It should be appreciated, as stated hereinabove, that the DAS chip 140 receives the signals generated by the photodiodes of the photodiode array 120 and converts the received signals such that further signal processing can be performed on the received signals to produce a medical image.

Figure 2:
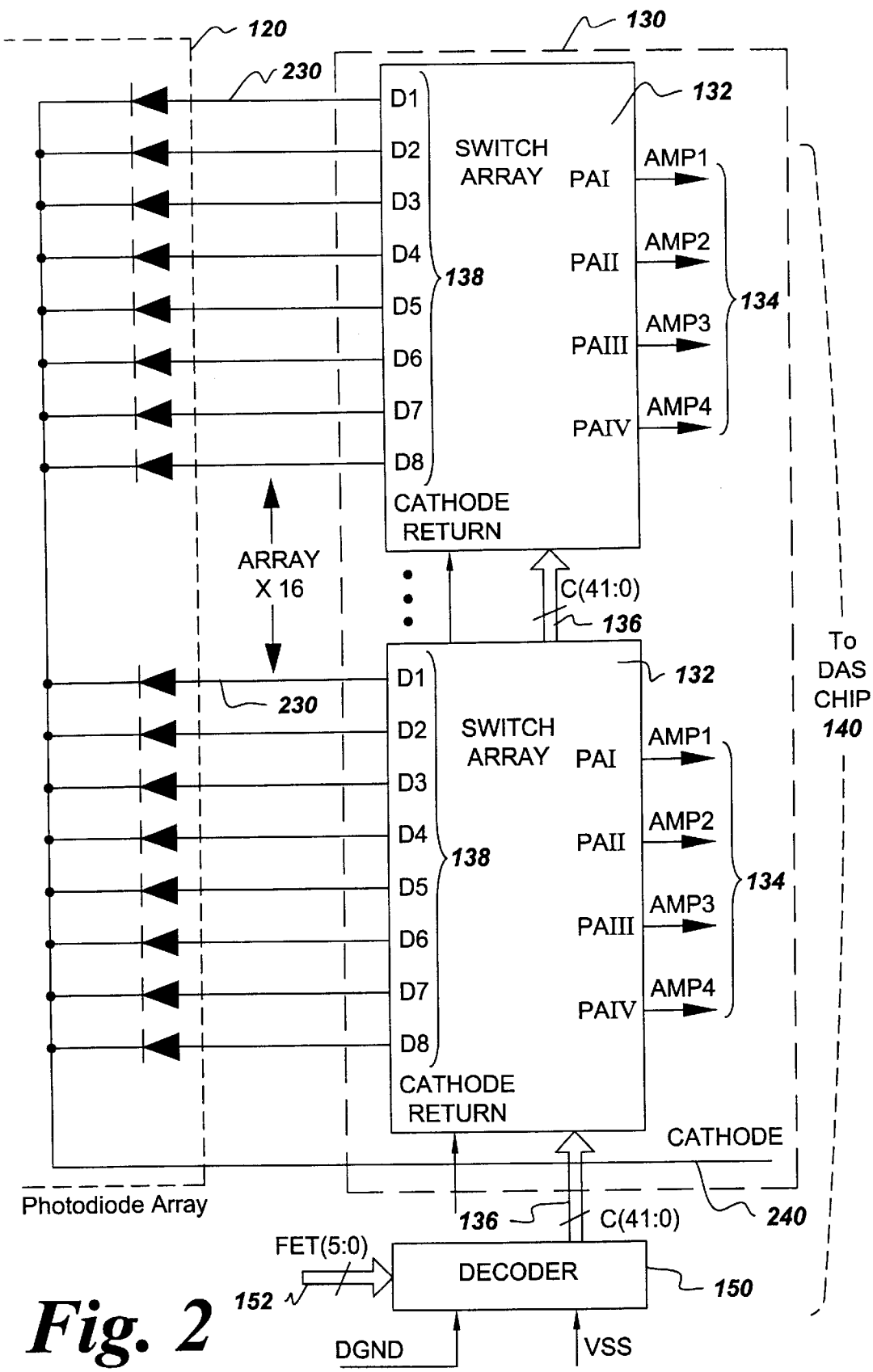
FIG. 2 is a schematic box diagram view of one embodiment of a plurality of switching arrays.

In one embodiment as shown in FIG. 2, the control signal output 152 includes five (5) control lines connected to decoder 150. The control output 136 connecting the decoder 150 to each of the switch arrays 132 comprises forty-one (41) control lines. The photodiode connection 138 that connects each of the switch arrays 132 to the photodiode array 120 has eight (8) control lines. It should also be appreciated that each of the photodiode connections 138 is connected via an output diode 230 to a cathode 240 of the photodiode array 120 of the detector 110. Further, in this embodiment, each of the switch arrays 132 is connected via switch array output 134 having four (4) control lines to the DAS chip 140.

Figure 3:
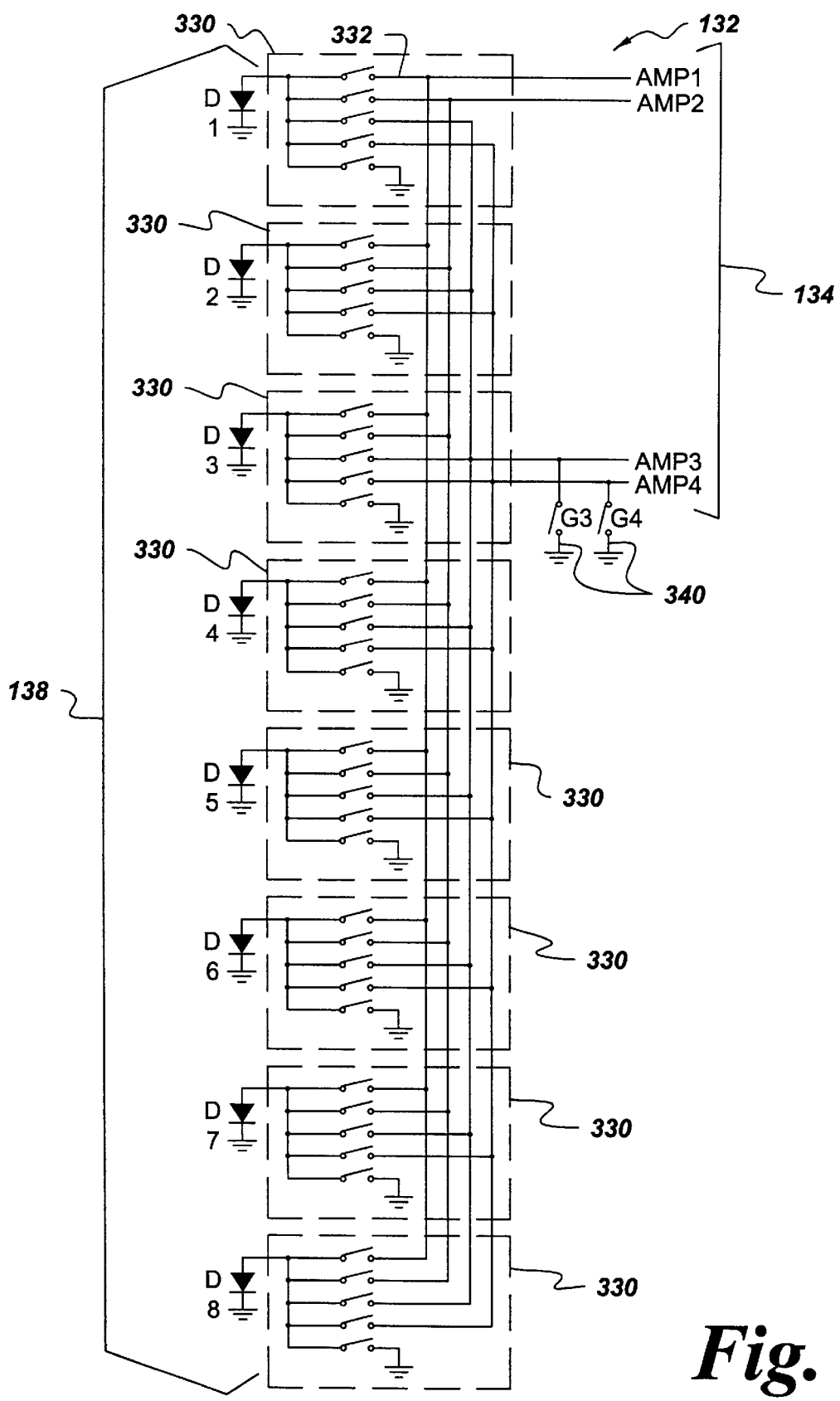
FIG. 3 is a schematic view of one embodiment of a switching array.

In one embodiment as shown in FIG. 3, a switch array 132 comprises a plurality of switches 332. In one exemplary embodiment, the switch array 132 comprises forty-two (42) switches. The plurality of switches 332 are arranged in a plurality of switching banks 330. In another exemplary embodiment, the switch array 132 comprises eight (8) switching banks 330. In one embodiment, each switch 332 comprises a field effect transistor (FET). In another embodiment, each switch 332 comprises p-type field effect transistor (pFET). Further, each switch bank 330 is connected to an output diode 230. The switches 332 and also the switching banks 330 are connected to switch array output 134. In one embodiment, the switch array output 134 comprises four (4) control lines. In addition, each switch array 132 has at least one array switch 340 that is also connected to the switch array output 134. As shown in FIG. 1, the switch array output 134 is connected to the DAS chip.

Figure 4:
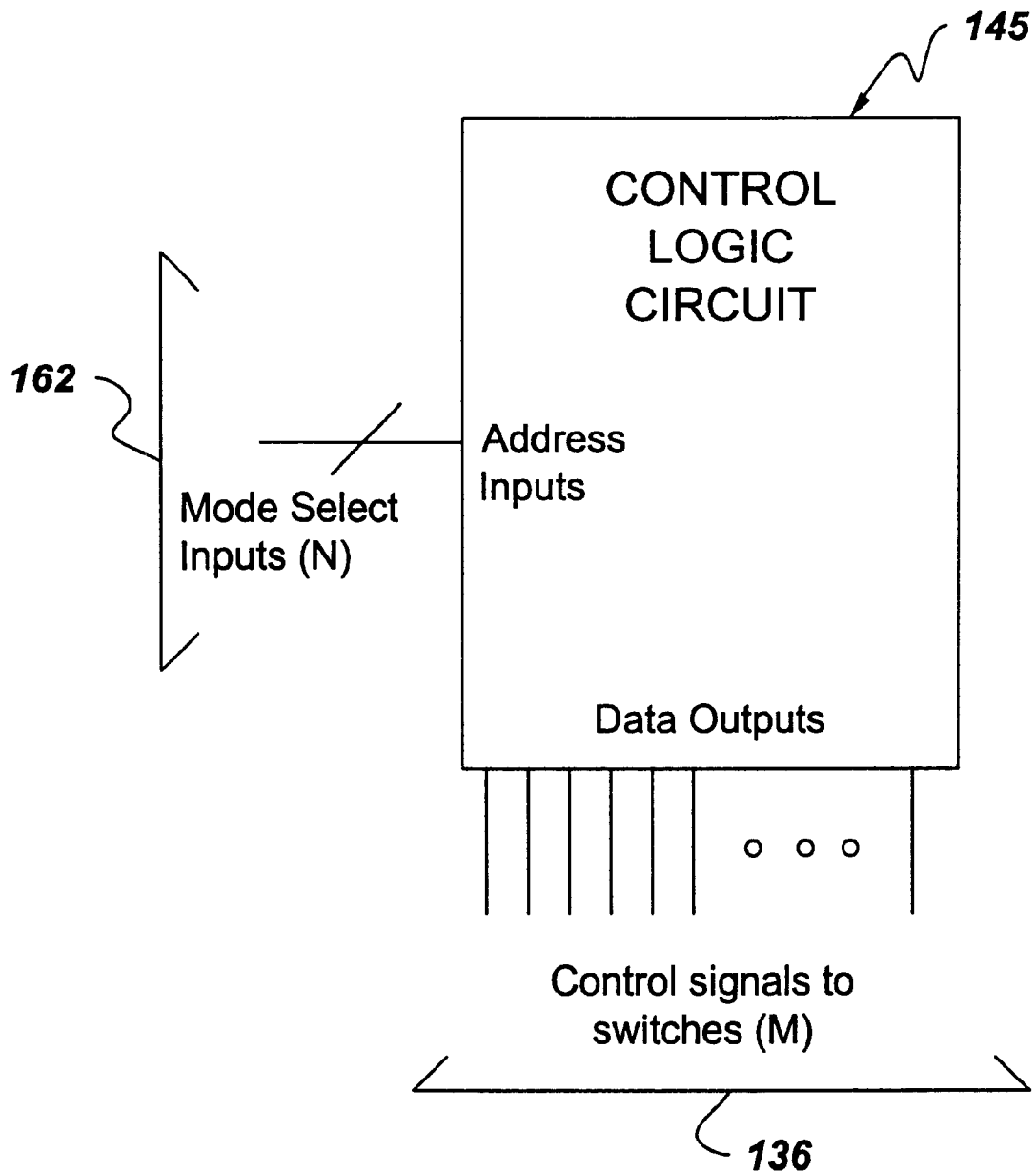
FIG. 4 is a box diagram view of one embodiment of a memory device.

In FIG. 4, a control logic circuit 145 includes mode select inputs 162 and control outputs 136. As shown in one embodiment in FIG. 1, the control logic circuit 145 can comprise a memory device 160 and a decoder 150. In this embodiment, the decoder 150 translates the stored switching configurations stored in the memory device 160 such that the switching configurations properly control the on/off state of each of the switches 332. In another embodiment, the decoder 150 translates the switching configuration stored in the memory device 160 such that each switch bank 332 in the switch array 132 is identically and/or similarly configured. In one exemplary embodiment, if the total number of mode select inputs 162 is N and the total number of control outputs 136 is M then the total number memory locations required in memory device 160 is $2^N \times M$ and where $2^N$ is the number of operational modes realizable with N mode select inputs 162.

Figure 5:
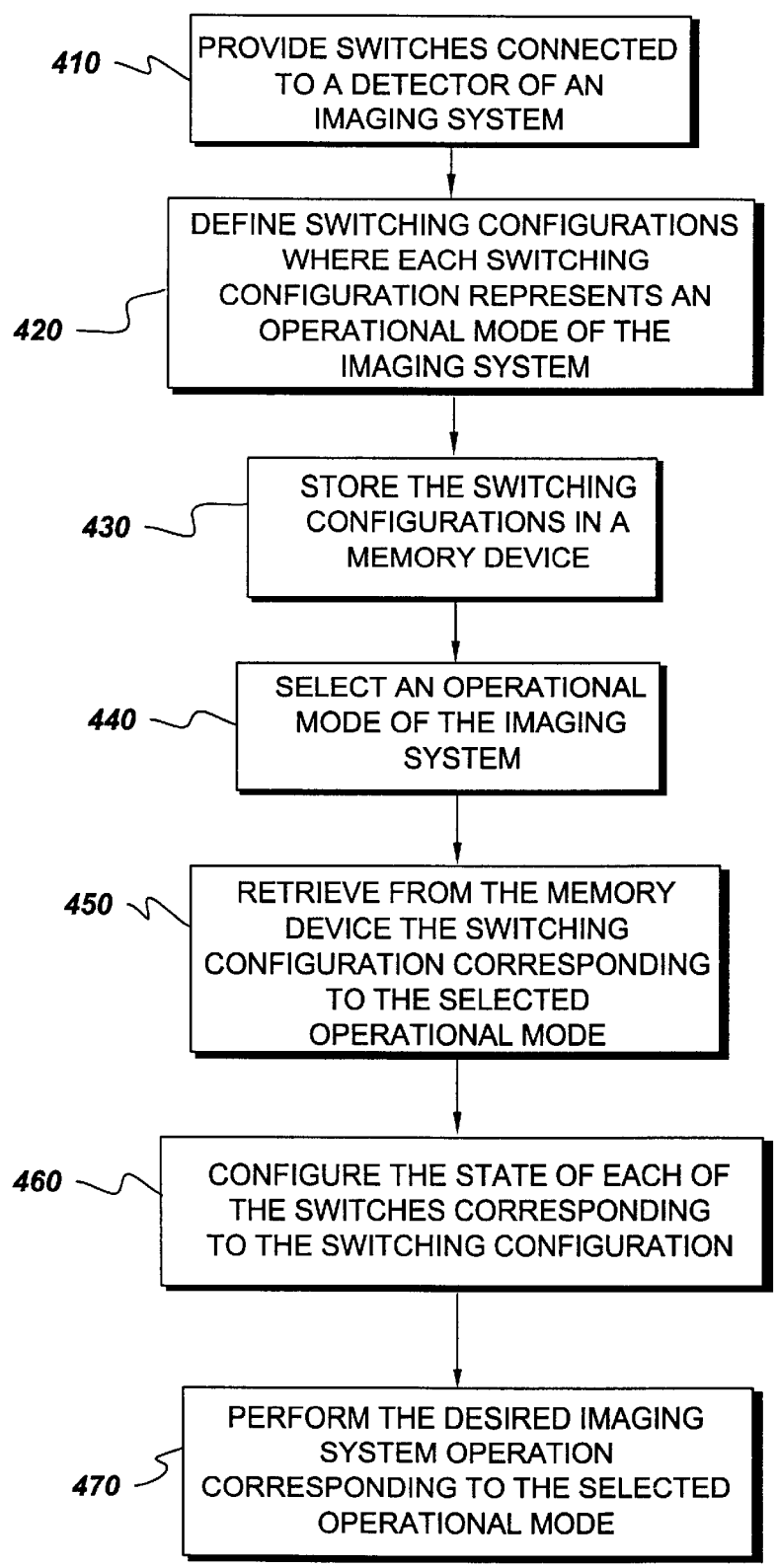
FIG. 5 is a flow diagram view of one embodiment of a method for selecting a slice thickness of a detector.

As shown in FIG. 5, one embodiment of a method for selecting a slice thickness of a detector 110 in an imaging system 100 is used to perform a desired operation by the imaging system 100. In one embodiment, the imaging system comprises a computed tomography (CT) imaging system. The method includes providing switches 332 that are connected to the detector 110 of the imaging system 100 (step 410). It should be appreciated that, in one embodiment, the switches 332 can be provided in switch banks 330 as shown in FIG. 3. It should also be appreciated that, in another embodiment, a switch 332 can comprise a field effect transistor (FET). A predetermined number of switching configurations is defined where each switching configuration represents an operation mode of the imaging system 100 (step 420). It should be appreciated that, in one embodiment, the switching configurations control the on/off states of each of the switches 332. In another embodiment, the on/off states of the switches 332 are configured via each switch bank 330 wherein each switch bank 330 is similarly and/or identically configured. It should also be appreciated that the operational modes of the imaging system 100 relate to various uses of the imaging system 100, such as, for example, experimental use, service use and imaging use.

The defined switching configurations are stored in a memory device 160 (step 430). In one embodiment, the memory device can comprises random access memory (RAM). In other embodiments, the memory device can comprise various other memory storage devices, such as, for example, a magnetic media, read-only memory (ROM), programmable read-only memory (PROM), erasable programmable read-only memory (EPROM), electrically erasable programmable read-only memory (EEPROM). An operational mode of the imaging system 100 is selected (step 440). It should be appreciated that a user of the imaging system 100, such as, for example, a medical doctor, a technician or other trained personnel, can select the operational mode via a user interface device (not shown). Once the operational mode has been selected (step 440), the switching configuration corresponding to the selected operational mode is retrieved from the memory device 160 (step 450). Using the retrieved switching configuration that corresponds to the desired operational mode, the state of each of the switches 332 is configured corresponding to the retrieved switching configuration (step 460). It should be appreciated that, in another embodiment, the states of the switches 332 can be controlled via each switching bank 330 wherein the switches 332 in each switching bank 330 have similar or identical switching configuration. Once the switches 332 have been configured according to the retrieved switching configuration, the desired imaging system 100 operation corresponding to the selected operational mode is performed (step 470). It should also be appreciated that the each switching configuration and, hence, each operational mode of the imaging system has a predetermined slice thickness of the detector 110. It should also be appreciated that, in one embodiment, the predetermined slice thickness can be different for each operational mode of the imaging system 100.

The foregoing discussion of the invention has been presented for purposes of illustration and description. Further, the description is not intended to limit the invention to the form disclosed herein. Consequently, variations and modifications commensurate with the above teachings and with the skill and knowledge of the relevant art are within the scope of the present invention. The embodiment described herein above is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. A detector device for use in an imaging system, the detector device comprising:
    a photodiode array positioned to detect radiation transmitted by the imaging system;
    a plurality of switch arrays connected to the photodiode array, each of the plurality of switch arrays having at least one output, each of the plurality of switch arrays comprises a plurality of switch banks wherein each of the plurality of switch banks comprising a plurality of switches; and
    a control logic circuit connected to the plurality of switch arrays and controlling a state of each of the plurality of switches in each of the plurality of switch banks based on a predefined switching configuration, the control logic circuit comprising a memory device being programmed to store a plurality of predefined switching configurations, each of the plurality of predefined switching configurations represents a respective operational mode of the imaging system wherein each respective operational mode has a respective predetermined detector slice thickness.

2. The detector device of claim 1 wherein each of the plurality of switches comprises a field effect transistor (FET).

3. The detector device of claim 2 wherein the FET comprises a pFET.

4. The detector device of claim 1 wherein the memory device is individually connected to each of the plurality of switches.

5. The detector device of claim 1 wherein the memory device comprises random access memory (RAM).

6. The detector device of claim 1 wherein the memory device comprises read-only memory (ROM).

7. The detector device of claim 6 wherein the ROM comprises programmable read-only memory (PROM).

8. The detector device of claim 6 wherein the ROM comprise erasable programmable read-only memory (EPROM).

9. The detector device of claim 6 wherein the ROM comprises electrically erasable programmable read-only memory (EEPROM).

10. The detector device of claim 1 wherein the plurality of switch arrays comprise 16 switch arrays and wherein the plurality of switch banks comprises 8 switch banks and wherein the plurality switches comprises 42 switches.

11. A detector device for use in an imaging system, the detector device comprising:
   a photodiode array positioned to detect radiation transmitted by the imaging system;
   a plurality switches connected to the photodiode array, the plurality of switches having at least one output, and
   a control logic circuit connected to the plurality of switches and controlling a state of each of the plurality of switches based on a predefined switching configuration, the control logic circuit comprising a memory device being programmed to store a plurality of predefined switching configurations, each of the plurality of predefined switching configurations represents a respective operational mode of the imaging system wherein each respective operational mode has a respective predetermined detector slice thickness.

12. The detector device of claim 11 wherein each of the plurality of switches comprises a field effect transistor (FET).

13. The detector device of claim 12 wherein the FET comprises a pFET.

14. The detector device of claim 11 wherein the memory device is individually connected to each of the plurality of switches.

15. The detector device of claim 11 wherein the memory device comprises random access memory (RAM).

16. The detector device of claim 11 wherein the memory device comprises read-only memory (ROM).

17. The detector device of claim 16 wherein the ROM comprises programmable read-only memory (PROM).

18. The detector device of claim 16 wherein the ROM comprise erasable programmable read-only memory (EPROM).

19. The detector device of claim 16 wherein the ROM comprises electrically erasable programmable read-only memory (EEPROM).

20. A method for selecting a slice thickness of a photodiode array of a detector in an imaging system, the method comprising:
   providing a plurality of switch arrays, each of the plurality of switch arrays comprising a plurality of switch banks wherein each of the plurality of switch banks comprises a plurality of switches, each of the plurality of switches is connected to the detector;
   defining a plurality of switching configurations wherein each of the plurality of switching configuration represents an operational mode of the imaging system wherein each of the plurality of switch banks are identically configured in a respective switching configuration;
   storing in a memory device a plurality of switching configurations, each of the plurality of switching configurations represents a respective operational mode of the imaging system wherein each respective operational mode has a respective predetermined detector slice thickness;
   selecting one of the plurality of operational modes of the imaging system;
   retrieving a corresponding switching configuration to the selected one of the plurality of operational modes; and
   configuring the state of each switch in each bank of each array according to the corresponding switching configuration.

21. The method of claim 20 further comprising the step of performing the selected one of the plurality of operational modes of the imaging system.

22. The method of claim 20 wherein each of the plurality of switches comprises a field effect transistor (FET).

23. The method of claim 22 wherein the FET comprises a pFET.

24. The method of claim 20 wherein the memory device comprises random access memory (RAM).

25. The method of claim 20 wherein the memory device comprises read-only memory (ROM).

26. The method of claim 25 wherein the ROM comprises a programmable read-only memory (PROM).

27. The method of claim 25 wherein the ROM comprises erasable programmable read-only memory (EPROM).

28. The method of claim 26 wherein the ROM comprises electrically erasable programmable read-only memory (EEPROM).

29. The method of claim 20 wherein the plurality of switch arrays comprise 16 switch arrays and wherein the plurality of switch banks comprises 8 switch banks and wherein the plurality switches comprises 42 switches.

30. A method for selecting a slice thickness of a photodiode array of a detector in an imaging system, the method comprising:
   providing a plurality of switches connected to the detector;
   defining a plurality of switching configurations wherein each of the plurality of switching configuration represents an operational mode of the imaging system;
   storing in a memory device a plurality of switching configurations, each of the plurality of switching configurations represents a respective operational mode of the imaging system wherein each respective operational mode has a respective predetermined detector slice thickness;
   selecting one of the plurality of operational modes of the imaging system;
   retrieving a corresponding switching configuration to the selected one of the plurality of operational modes; and
   configuring the state of each of the plurality of switches according to the corresponding switching configuration.

31. The method of claim 30 further comprising the step of performing the selected one of the plurality of operational modes of the imaging system.

32. The method of claim 30 wherein each of the plurality of switches comprises a field effect transistor (FET).

33. The method of claim 32 wherein the FET comprises a pFET.

34. The method of claim 30 wherein the memory device comprises random access memory (RAM).

35. The method of claim 30 wherein the memory device comprises read-only memory (ROM).

36. The method of claim 35 wherein the ROM comprises a programmable read-only memory (PROM).

37. The method of claim 35 wherein the ROM comprises erasable programmable read-only memory (EPROM).

38. The method of claim 36 wherein the ROM comprises electrically erasable programmable read-only memory (EEPROM).

39. The method of claim 30 wherein the plurality of switches are arranged in a plurality of switch arrays, each of the switch arrays having a plurality of switch banks, each of the switching banks comprising a predetermined number of the plurality of switches.

* * * * *